(12) United States Patent
Al-Bin-Mousa et al.

(10) Patent No.: US 10,883,908 B2
(45) Date of Patent: Jan. 5, 2021

(54) STAGE FOR HIGH TEMPERATURE INDENTATION TEST

(71) Applicant: KING FAHD UNIVERSITY OF PETROLEUM AND MINERALS, Dhahran (SA)

(72) Inventors: Jafar Al-Bin-Mousa, Dhahran (SA); Ahmad Al-Ghamdi, Dhahran (SA); Kamal Al-Shareef, Dhahran (SA); Abdulrahman Al-Adsani, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 304 days.

(21) Appl. No.: 15/919,986

(22) Filed: Mar. 13, 2018

(65) Prior Publication Data

US 2018/0259436 A1 Sep. 13, 2018

Related U.S. Application Data

(60) Provisional application No. 62/470,663, filed on Mar. 13, 2017.

(51) Int. Cl.
*G01N 3/42* (2006.01)
*G01N 3/18* (2006.01)
(Continued)

(52) U.S. Cl.
CPC ............... *G01N 3/42* (2013.01); *F01D 5/288* (2013.01); *F01D 25/285* (2013.01); *G01N 3/18* (2013.01);
(Continued)

(58) Field of Classification Search
CPC .... G01N 3/42; G01N 3/54; G01N 2203/0078; G01N 2203/0226; G01N 2033/0003;
(Continued)

(56) References Cited

U.S. PATENT DOCUMENTS 5,361,641 A 11/1994 Eldridge et al.
2007/0180897 A1* 8/2007 Dankert ................ F01D 21/003
73/112.01

(Continued)

FOREIGN PATENT DOCUMENTS

CN 102759485 B 3/2014
CN 203732383 U 7/2014
(Continued)

*Primary Examiner* — Herbert K Roberts
*Assistant Examiner* — John M Royston
(74) *Attorney, Agent, or Firm* — Oblon, McClelland, Maier & Neustadt, L.L.P.

(57) ABSTRACT

An indentation tester and indentation method for testing a sample heated at a temperature range from above 800° C. to 1200° C., and above, is disclosed. The indentation tester includes a stage having a metallic cylindrical base that houses an inner cylindrical base made of a temperature resistant material sufficient to maintain shape over the range of the heating temperature. A removable crown fastens to the cylindrical base and includes a ring that holds an axisymmetric pipe made of a temperature resistant material sufficient to maintain shape over the range of heated temperature. A nut is turned to tighten the pipe which secures the sample and guides an indenter to penetrate the sample. The indenter includes a rod made of temperature resistant material and a indenter tip.

9 Claims, 23 Drawing Sheets

(51) Int. Cl.
  *G01N 19/04* (2006.01)
  *G01N 3/54* (2006.01)
  *F01D 25/28* (2006.01)
  *G01N 33/00* (2006.01)
  *F01D 5/28* (2006.01)

(52) U.S. Cl.
  CPC ............... *G01N 3/54* (2013.01); *G01N 19/04* (2013.01); *F05D 2230/40* (2013.01); *F05D 2230/90* (2013.01); *G01N 2033/0003* (2013.01); *G01N 2203/0078* (2013.01); *G01N 2203/0226* (2013.01)

(58) Field of Classification Search
  CPC ...... F01D 25/285; F01D 5/288; F01D 21/003; F05D 2230/40; F05D 2230/90; F05D 2260/83; F05D 2260/80
  See application file for complete search history.

(56) References Cited

U.S. PATENT DOCUMENTS

| | | | | |
|---|---|---|---|---|
| 2014/0078299 | A1* | 3/2014 | Kataoka | G01N 3/42 348/137 |
| 2014/0224003 | A1* | 8/2014 | Zhang | G01N 3/42 73/82 |
| 2015/0064439 | A1* | 3/2015 | Maeno | G01N 3/42 428/293.7 |
| 2016/0169718 | A1* | 6/2016 | Dama | G01Q 70/02 73/1.01 |

FOREIGN PATENT DOCUMENTS

| | | | |
|---|---|---|---|
| CN | 105466773 | A | 4/2016 |
| CN | 106226152 | A | 12/2016 |
| CN | 106404574 | A | 2/2017 |
| JP | 2013101105 | A * | 5/2013 |
| KR | 941172 | B1 | 2/2010 |

* cited by examiner

STAGE FOR HIGH TEMPERATURE INDENTATION TEST

CROSS-REFERENCE TO RELATED APPLICATIONS

This application claims the benefit of priority to provisional application No. 62/470,663 filed Mar. 13, 2017, the entire contents of which are incorporated herein by reference.

FIELD OF DISCLOSURE

The present disclosure relates generally to a stage for high temperature indentation testing that may be used, for example, for indentation testing at a high temperature such as greater than or equal to 1200° C.

BACKGROUND

Machines like gas turbines operate at temperatures of 1200° C., or more. To aid in operating at these high temperatures, turbine blades are coated with a thin (nearly 150 microns in thickness) material called a Thermal Barrier Coating (TBC). Understanding the mechanical behavior of the material at such high temperature is required for design and durability analyses. Micro-indentation tests and nano-indentation tests are types of tests that can be used to characterize the mechanical behavior (e.g., hardness, fracture toughness, scratch hardness, and wear properties) of thin films such as TBC.

Both a micro-indentation test and a nano-indentation test require a special indenter (usually made of a very hard material like diamond or sapphire) to be pressed into a sample whose properties are to be determined. Both a micro-indentation test and a nano-indentation test require the tip of the indenter to be of a special geometry (e.g., pyramid, wedge, cone, cylinder, sphere). In each type of test, the sample must be gripped on a testing stage as the indenter tip contacts or penetrates it. However, several challenges arise if the test is to be performed at high temperatures such as 800° C. to 1200° C., or more, that are required for testing of TBC.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
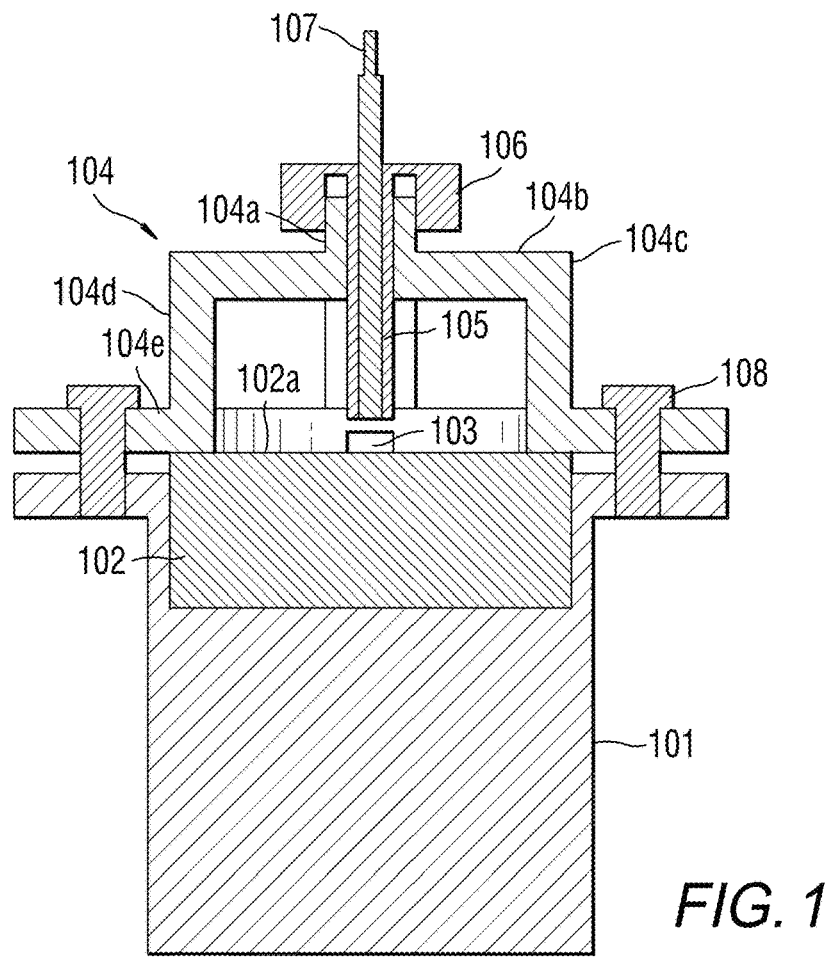
FIG. 1 is a schematic that shows a stage, according to an exemplary aspect of the disclosure.

Referring now to the drawings, wherein like reference numerals designate identical or corresponding parts throughout several views, the following description relates to a stage for high temperature indentation testing.

An indenter stage is disclosed for performing a micro-indentation test or a nano-indentation test that can be used to characterize the mechanical behavior of thin films such as TBC at a high temperature such as 800° C. to 1200° C., or more. The stage may include a base that houses a thin base made of a high temperature resistant material on which a specimen, also referred to as a sample, is placed for testing. A crown, which can be fastened to the base, clamps to the thin base to grip and hold the thin base in place while a heating source (such as a metal heating element including an induction heating coil, ceramic heating element, and/or gas heater, or the like) is used to heat the sample to the high temperature and the indenter penetrates the sample. The crown facilitates the clamping of the sample through its threaded portion which a nut is tightened to in order to push a pipe against the sample (as a result clamping it). The sample, and anything below it (the heat resistant material 102 and the base 101), must behave as a rigid single piece in order for the system to be compliant. In another words, if the sample and/or the heat resistant material are placed on top of each other without any clamping force the acquired signal from the test will be faulty/incorrect). Therefore, clamping of all pieces is very critical for getting accurate experimental results.

A sample for a micro-indentation test may be a few microns in thickness and may be any width that is at least as large as the size of the tip of the indenter. Although the sample may be any material for which hardness, or other mechanical or physical properties, is to be determined, the disclosed high temperature micro-indentation test is primarily for thermal barrier coating materials for turbine blades. Turbine blades are usually made of super alloy (nickel/cobalt based material). This super alloy is coated with a ceramic based material that consists of a bond coat and top coat. Sometimes the thermal barrier coating (TBC) refers to the ceramic materials (bond and top coats). Otherwise, the super alloy and the ceramic (top and bond coats) are referred to as TBC or TBC system.

FIG. 1 is a schematic of an indenter stage according to an exemplary aspect of the disclosure. In one embodiment, the indenter stage may be about 20 cm in height and about 16 mm in width. However, embodiments may be 8 to 10 cm in height and 12-15 cm in width. In one or more embodiments, the indenter stage may include a crown 104, which has a threaded ring 104a in the center and evenly distributed spokes 104b extending to an outer rim 104c. The threaded ring 104a, spokes 104b, and outer rim 104c provide support and position an indenter 107. Although the embodiment includes a circular outer rim 104c, the outer rim may be any shape that has a geometric center for the threaded ring 104a. In some embodiments, the outer rim 104c may be formed of straight line edges, such as a triangle, a square, a pentagon, a hexagon, or an octagon. The number of spokes 104b can two or more, which are evenly distributed by the same angle. The outer rim 104c extends to a lower rim portion 104e that fastens to the metallic cylindrical base. The lower rim 104e may be of the same shape as the outer rim 104c. The connection between the outer rim 104c and the lower rim portion 104e may be by way of legs 104d that correspond in position to the spokes. Although the outer rim 104c is shown as being connected to the lower rim portion 104e by legs 104d, it is understood that the legs 104d may be replaced with a wall that extends substantially over a majority of the lower surface of the outer rim 104c, e.g., a cylindrical wall. As described above, the crown 104 holds the heat resistant material 102 in place and facilitates clamping of a sample 103 through a nut-thread-pipe arrangement. Also, the crown 104 holds an indenter 107. Because the crown 104 is for holding the indenter 107 and may be exposed to high heat during a high temperature indentation test, the crown 104 is preferably made of a material that can withstand heat at high temperatures, for example in a range of about 300 to 500° C., and remain rigid without becoming deformed.

The indenter 107 for performing the indentation slides within a pipe 105, which passes through the threaded ring 104a. The indenter 107 consists of two parts: a holder which is a long cylindrical rod, and an indentation tip (or insert) which is typically made of diamond with pyramid, wedge, cone, cylinder or sphere shape. The indentation tip (or insert) is attached to the holder (the long rod) which must be made of high temperature resistant material like ceramic by threading or any other temporary joining method. The holder is actuated by a force application device.

A nut 106 is threaded from inside and is placed on the top of the ring 104a to tighten the pipe 105. The pipe 105 must be made of special heat resistant material such as ceramics. As the pipe being pushed downward it pushes the sample against the heat resistant base (102). This provides clamping of the sample. An important advantage is that the amount of clamping force exerted on the sample can be manipulated by the rotation of the nut. However, the friction between the nut and the pipe may cause the pipe to rotate. This rotation is not needed, and it may cause some undesirable effects on the sample. Therefore, the internal surface of the nut which is in contact with the pipe may be covered with low friction material (like Teflon) or a bearing can be mounted there. In an exemplary aspect, the nut 106 may be turned by a motor. Also, the motor may include a motor control device. Another exemplary aspect is an automatic actuator that pushes the tube.

A base 102 in the shape of a cylindrical disc is housed in the metallic cylindrical base 101. The sample 103 is placed on the cylindrical disc 102, which can sustain a high temperature. A top portion 102a of the cylindrical disc is slightly elevated above the top of the metallic cylindrical base 101 to an extent that the crown 104 can tighten the cylindrical disc 102. The crown 104 may be attached to a stage 101 by one or more bolts (or other fastening means) 108 for ease of access to and replacement of the sample and cylindrical base 102. The bolts may be tightened by a nut. Alternatively, the holes for the bolts may be threaded, so that tightening is made by turning the bolt inside the hole. Any fastening means to attach the crown 104 to the stage 101 must be such that no lateral movement of the crown occurs during indentation testing. It may be possible to fasten the crown 104 to the stage 101 by clamps, such as a vice clamp having a cone-shaped end that can be inserted into the bolt hole.

A heating source (such as a metal heating element including an induction heating coil, a ceramic heating element, or a gas heater) may be used to heat the sample to temperatures up to and including 1200° C., or more.

Figure 2:
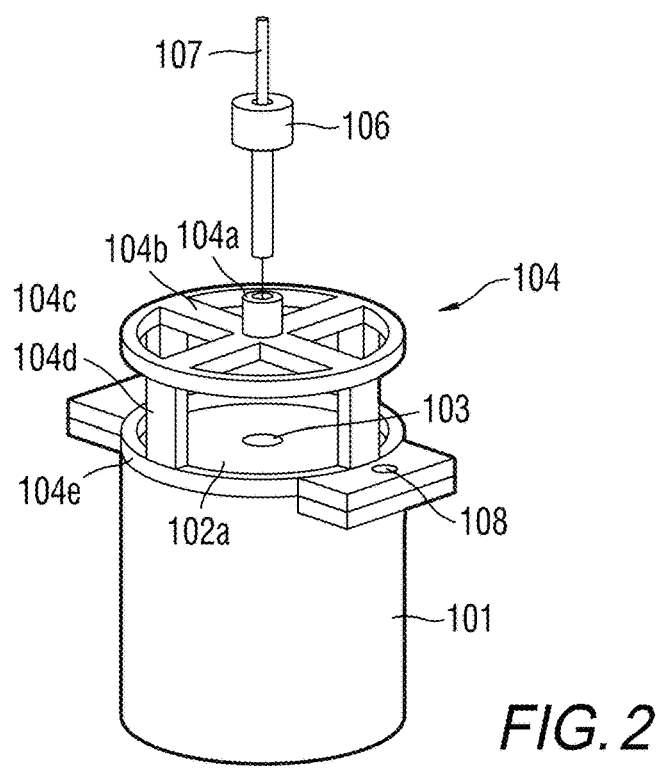
FIG. 2 is a perspective view that shows a first configuration according to one example.

FIG. 2 is a perspective view of an example configuration of the indenter stage of FIG. 1. In one or more embodiments, the indenter stage includes a metallic cylindrical base 101 that houses a cylindrical disc 102 made of high temperature resistant material. Although the base 101 and disc 102 are cylindrical, the indenter stage is not limited to this shape. The cylindrical shape is uniform, which simplifies the design of the indenter stage. Other shapes such as cube, or shapes with polygonal bases, are possible. The crown 104 is fastened to the metallic cylinder 101, and in this position secures the cylindrical disc 102 (of temperature resistant material) so that the sample 103 can be heated to a high temperature in a range of 800° C. to 1200° C., or more, while the indenter 107 contacts or penetrates the sample 103. The high temperature resistant material may be a material that can withstand a temperature that is sufficient to melt most metals. Some known high temperature resistant materials include Niobium, Molybdenum, Tantalum, Tungsten, Rhenium, and alloys thereof which have a melting point that is more than 1500° C. High temperature resistant materials also include ceramics. Although ceramic materials are brittle and are weak under tension, they perform well under compression and are abundantly available. In embodiments, components that are subject to high temperatures are only subject to compression, components including the cylindrical base are preferably made of ceramic material such as an inorganic ceramic material.

The cylindrical base 101 that houses the cylindrical disc 102 is rigid such that force applied by the indenter 107 while the sample 103 is heated to high temperature does not cause the cylindrical disc 102 to be displaced. A pipe 105 is tightened against the sample 103 by the nut 106 in order to grip and hold the sample 103 in place during indentation testing. The pipe 105 is also of a high temperature resistant material so that a constant clamping force is applied to hold the sample 103 in place during indentation testing under high temperature conditions.

The sample 103 preferably has parallel top and bottom surfaces, and preferably must be kept parallel to the top and bottom surfaces as much as possible. The area of the top surface of the sample may be macro size (i.e., 1000 microns or greater) in order to perform multiple indentations in different locations and to allow for easy gripping. The impression made by an indenter tip may not exceed 35 microns. Thus, the thickness of the sample 103 should be sufficient to accommodate a 35 micron impression. For example, a sample 103 may be one inch square with a thickness of about a half inch. This thickness includes the base material, like a super alloy (or substrate) and the coating (on top of the base material). The coating itself can be composed of different layers such as bond coat and a top coat.

In one embodiment, the crown 104 is arranged with a threaded ring 104a positioned above the top surface of the disc 102 by a distance that is based on the size of the pipe 105. The pipe 105 must be shorter than the indenter holder 107. The length of the indenter holder 107 will set the distance between the sample (which is heated to 1200° C. or more) and the actuator (and other electronics and parts of the indentation equipment), thus, keeping away from the heat. However, this is not always the case. For example, if the entire apparatus is placed in a vacuum chamber, then only radiation heat transfer is going to be operative (no convection because there is no air). In that case, a shield can be used to protect the electronics from the heat. The length of the pipe 105 should be long enough to allow fixing the sample in place while it is heated at a high temperature. An outer rim 104c connects to the ring 104a by two or more spokes 104b extending from the threaded ring 104a at equal angles between adjacent spokes. The outer rim 104c is mounted above the disc 102 by two or more legs 104d corresponding to the spokes 104b. A lower rim portion 104e clamps the disc 102. Although two bolts 108 are used in this example, there may be four or more bolts, or other fastening means, for bolting/fastening each leg 104d of the crown.

Figure 3:
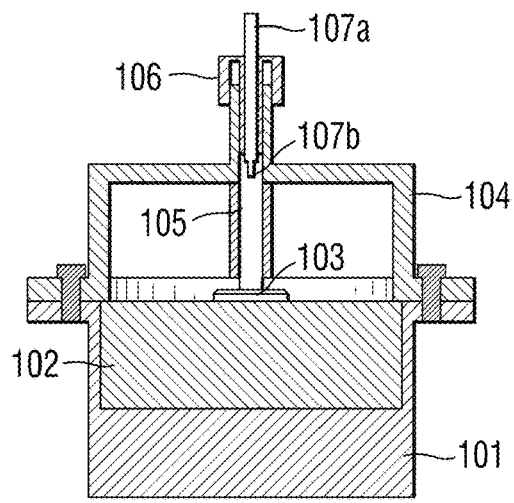
FIG. 3 is a schematic of the first configuration in FIG. 2 having a shorter base.

FIG. 3 is a cross-section of the example configuration of the indenter stage of FIG. 2 configured with a shorter base. Indenting may be performed by an indenter 107. The pipe 105 may be clamped by a nut 106 that is attached to the crown 104. The pipe 105 passes through the crown ring 104a which applies compressing force to the sample 103 to ensure the sample does not slide during the indentation test. The pipe 105 enables a high temperature resistant rod to pass through and slide within the pipe 105. For purposes of micro-indentation or nano-indentation testing, the high temperature resistant rod has a diamond attached to one end of the rod, which together constitute the indenter 107.

Figure 4A:
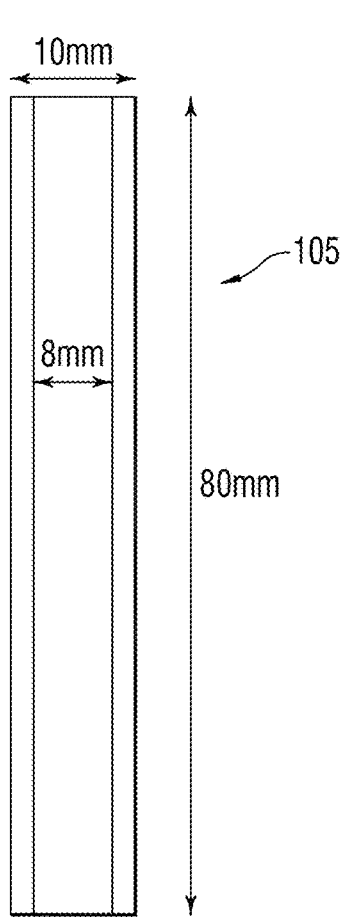
FIG. 4A illustrates a pipe of an indenter stage according to an exemplary aspect of the present disclosure.
Figure 4B:
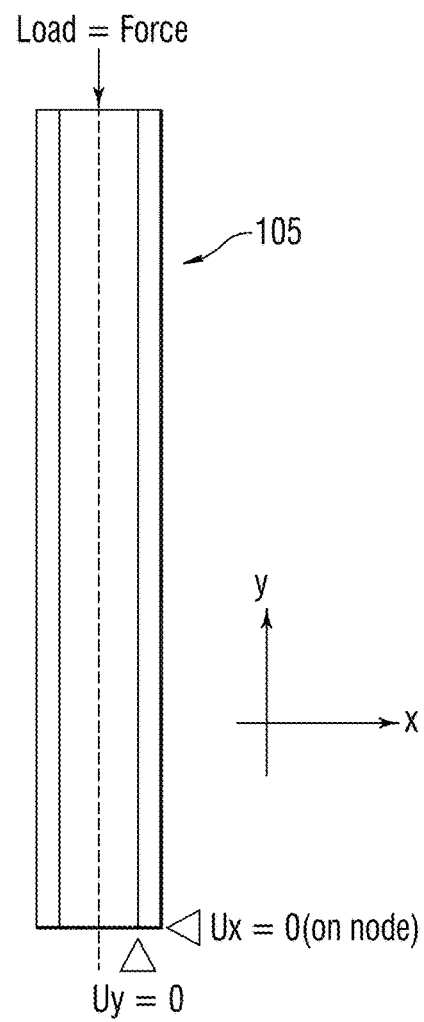
FIG. 4B illustrates loading and boundary conditions of a pipe of an indenter stage according to an exemplary aspect of the present disclosure.

FIGS. 4A and 4B describe schematics of the pipe 105. The nut 106 (FIG. 3) when tightened applies a compressive force to the pipe 105. In an exemplary aspect, the pipe 105 is axisymmetric and is made of a ceramic material. The ceramic material performs well under compression and the axisymmetric configuration of the pipe allows a uniform application of the compression force. In an exemplary embodiment, a ceramic pipe 105 having a length that is about ten times the diameter is sufficient to handle a compression load that would be applied by the nut 106.

Figure 5:
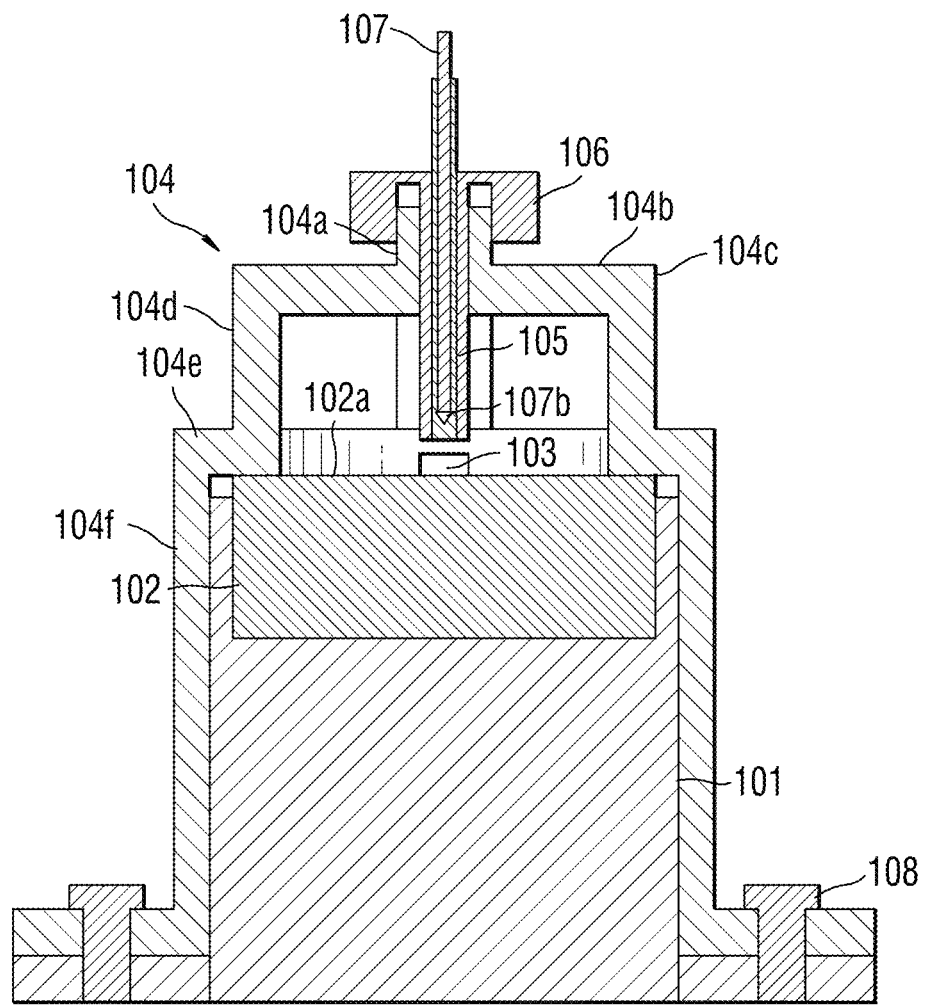
FIG. 5 is a schematic of a second configuration of the indenter stage having an alternative bolting configuration according to an exemplary aspect of the disclosure.

FIG. 5 is a schematic of indenter stage having an alternative bolting configuration according to an exemplary aspect of the disclosure.

Figure 6:
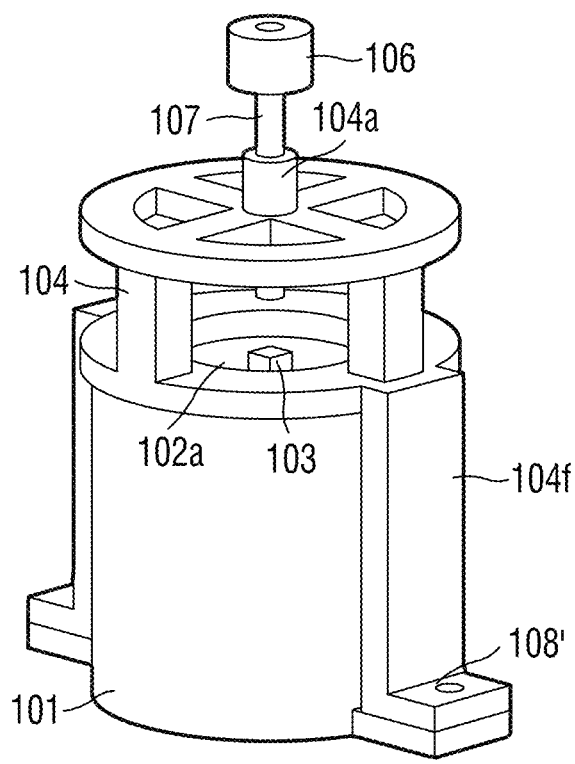
FIG. 6 is a perspective view of the second configuration of FIG. 5.
Figure 7:
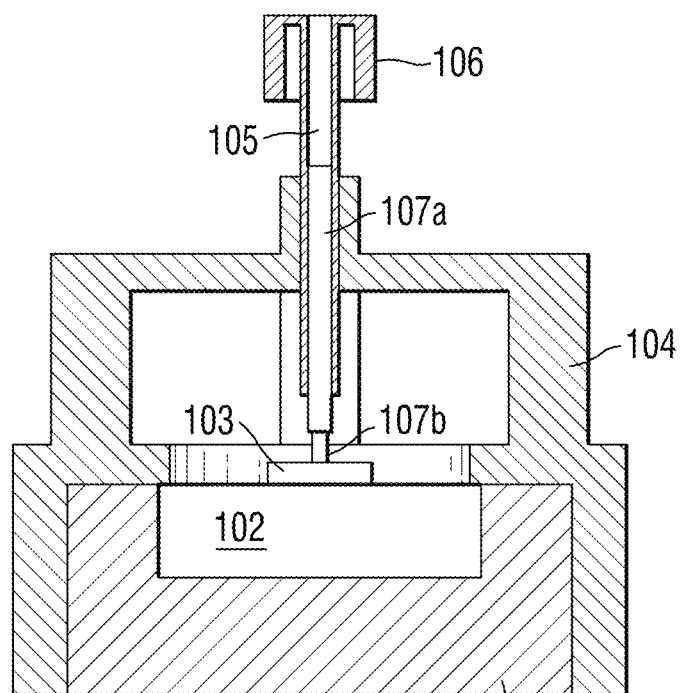
FIG. 7 is a schematic of the second configuration in FIG. 5 having a shorter base.

FIG. 6 is a perspective view of the alternative bolting configuration for the indenter stage of FIG. 5. FIG. 7 is a schematic of the example configuration in FIG. 5 having a shorter base. As can be seen in FIG. 2, the crown 104 may be attached to a section at the top of the stage 101 by one or more bolts 108. As can be seen in in FIG. 6, the crown 104 may be attached to a lower portion of the stage 101 by one or more bolts 108'.

In an exemplary aspect, both the pipe 105 and disc 102 are made of a ceramic material. The use of ceramic material for the pipe and the disc enables the sample 103 to be heated to 1200° C. while performing highly accurate indentation testing. Also, as mentioned above, ceramic material does well in handling compression load.

Figure 8:
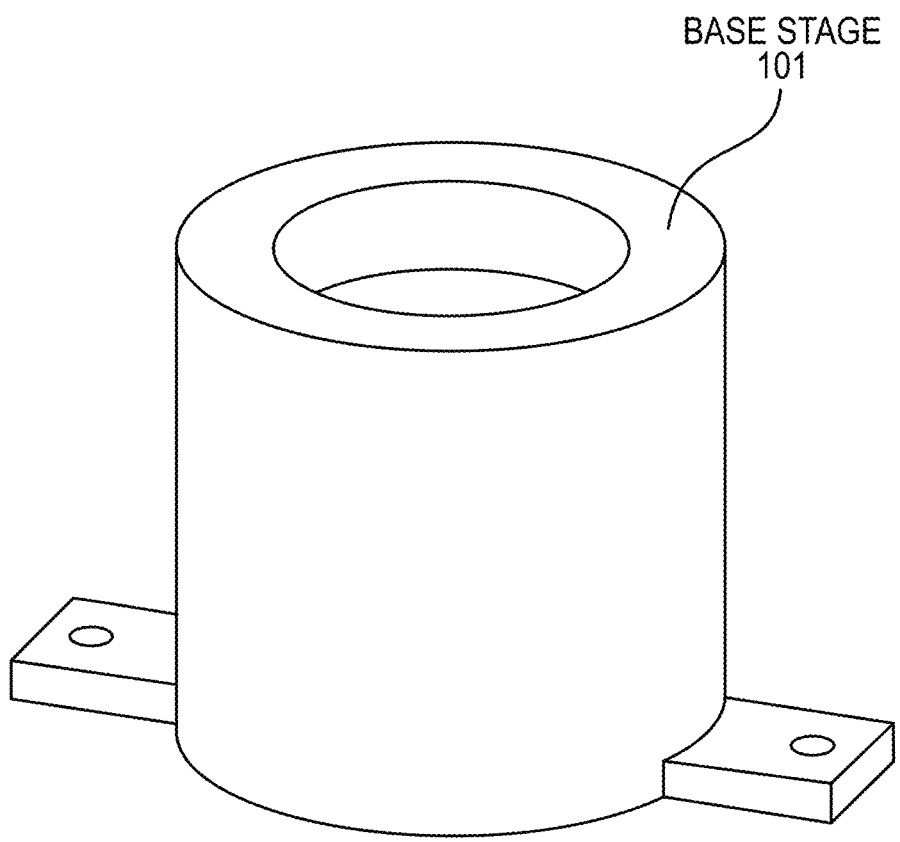
FIG. 8 is a perspective view of a cylindrical base having the configuration of FIG. 5.
Figure 9:
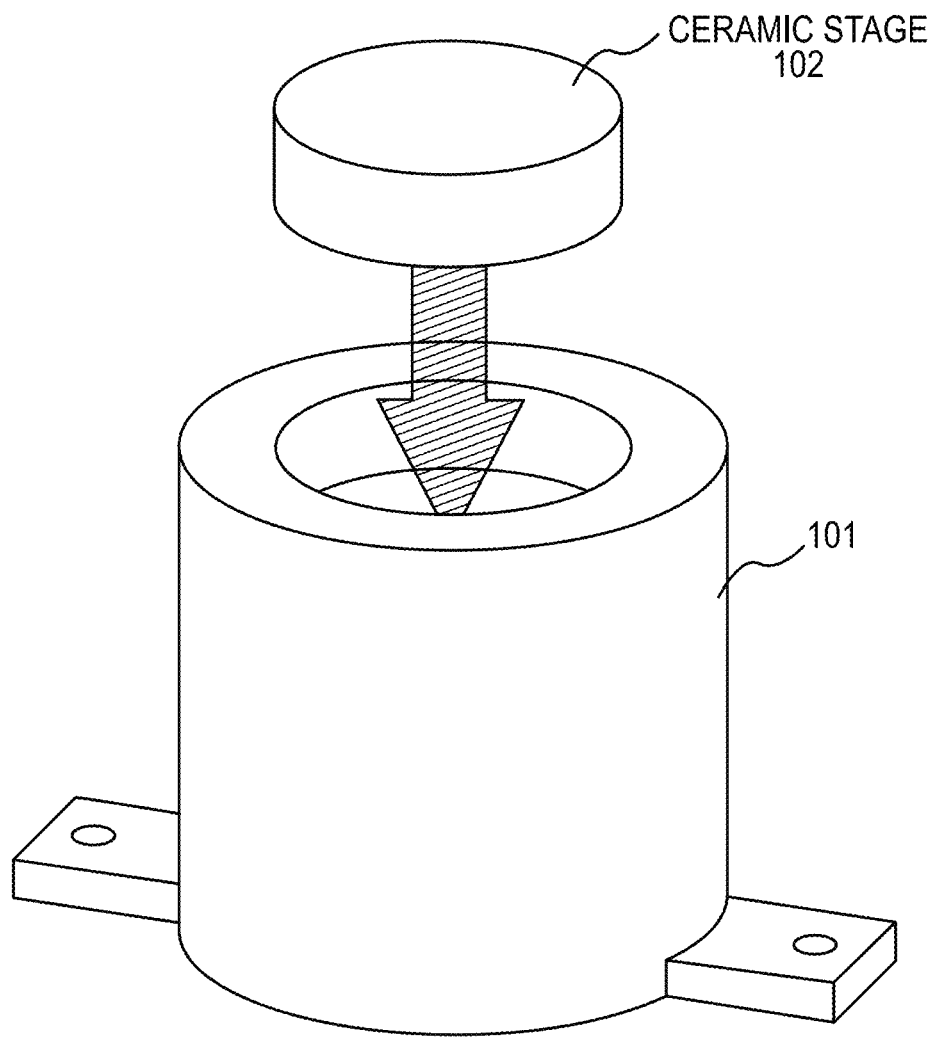
FIG. 9 is a perspective view of the cylindrical base illustrating a location where the thin cylindrical base will be inserted.
Figure 10:
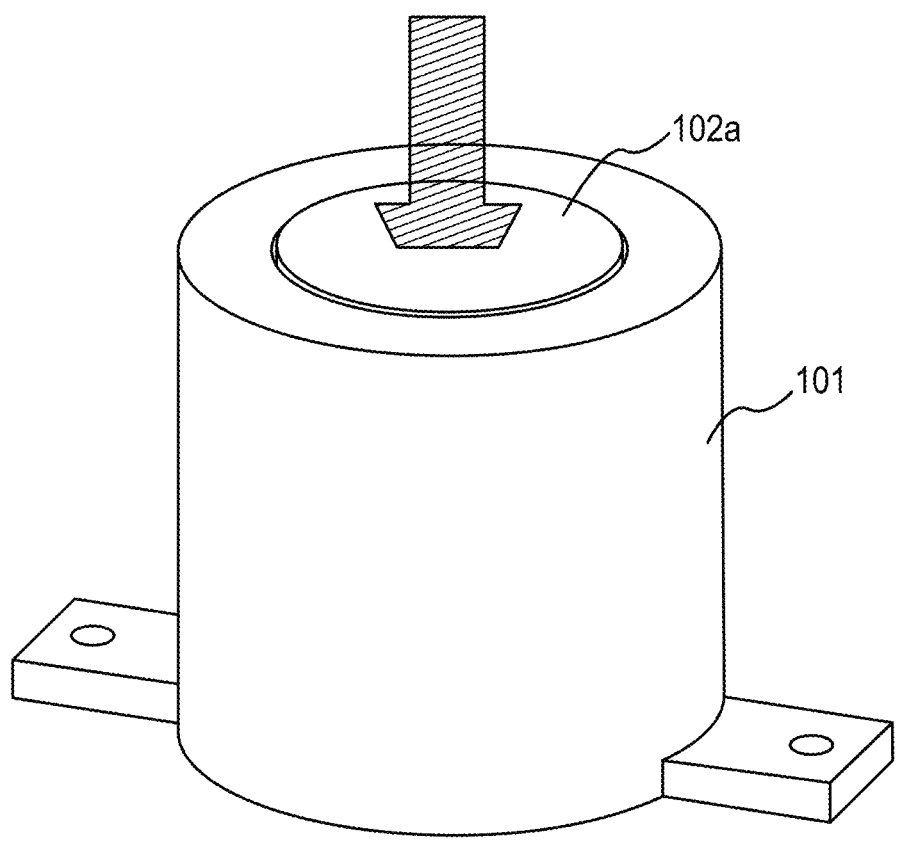
FIG. 10 is a perspective view of the cylindrical base illustrating the inserted thin cylindrical base.
Figure 11:
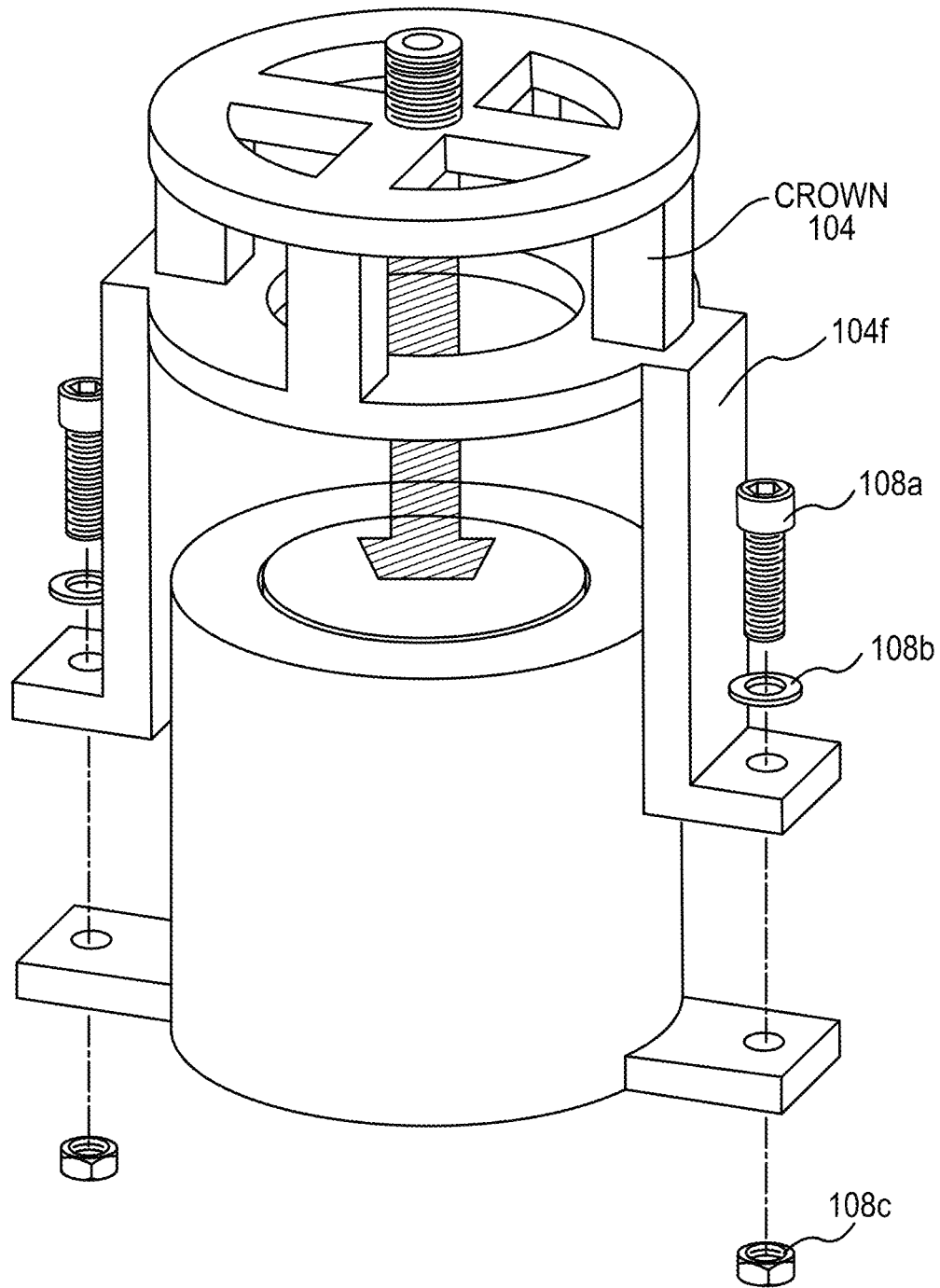
FIG. 11 is a perspective view of the crown for connection to the cylindrical base.
Figure 12:
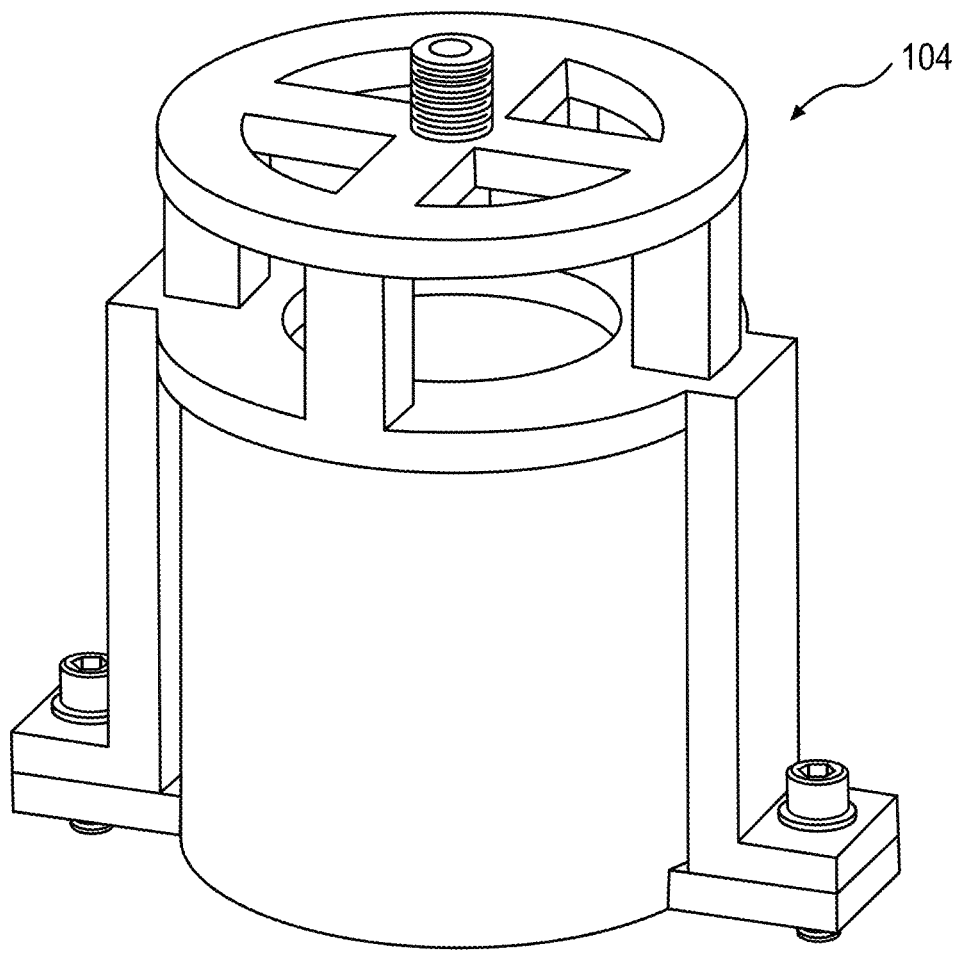
FIG. 12 is a perspective view of the crown mounted to the cylindrical base.
Figure 13:
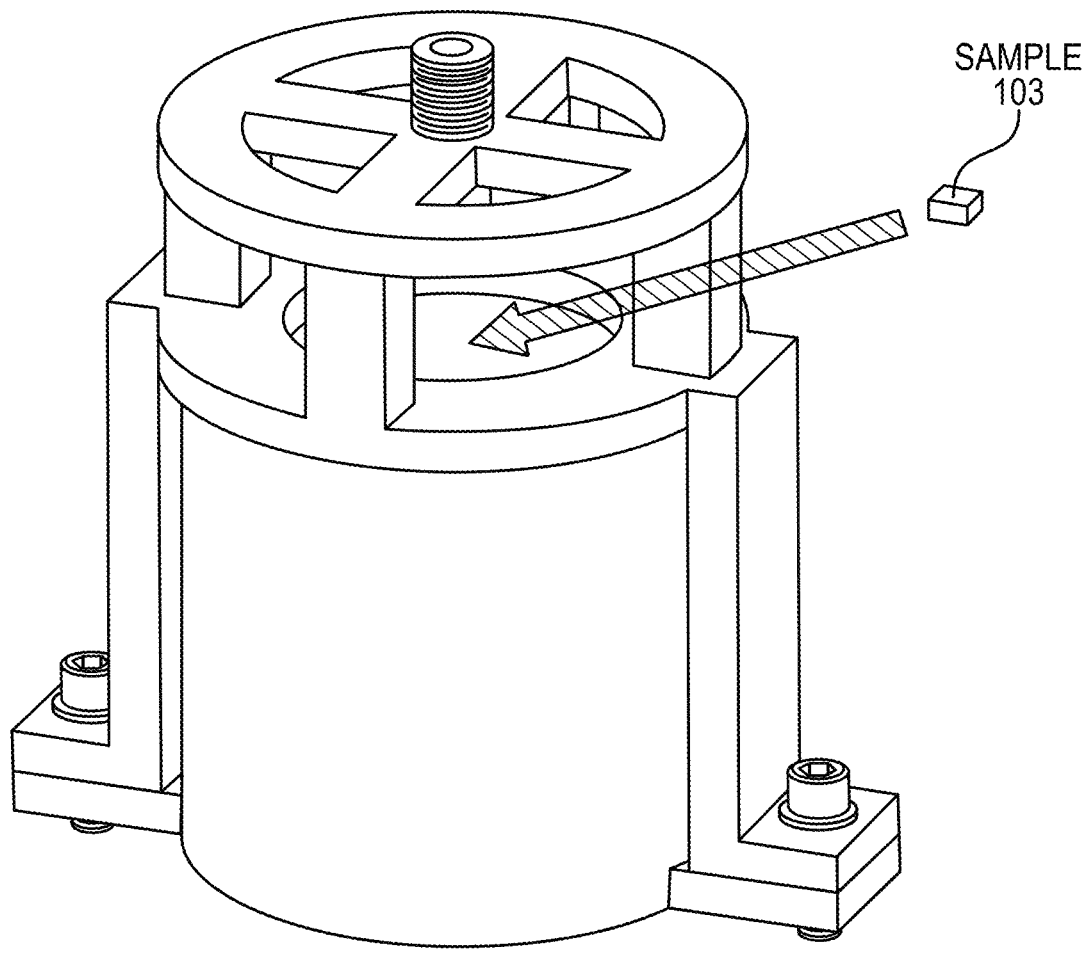
FIG. 13 is a perspective view of indenter stage while placing a sample according to an exemplary aspect of the disclosure.
Figure 14:
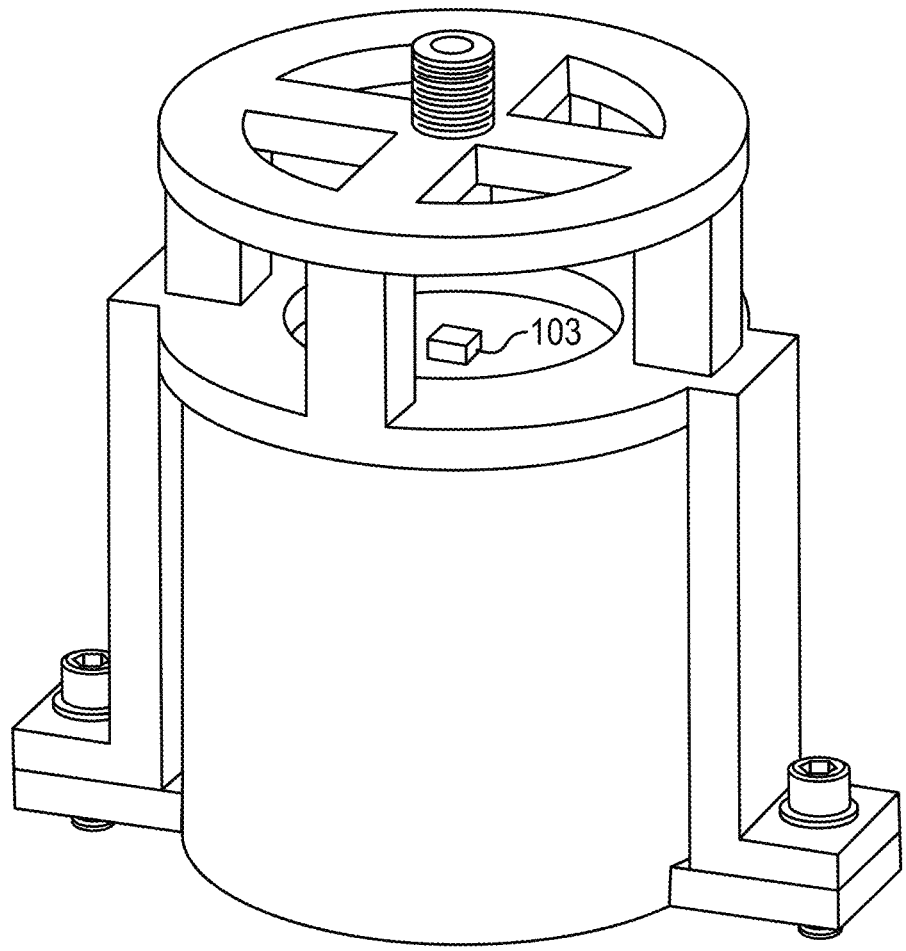
FIG. 14 is a perspective view of the indenter stage having the sample in place according to an exemplary aspect of the disclosure.
Figure 15:
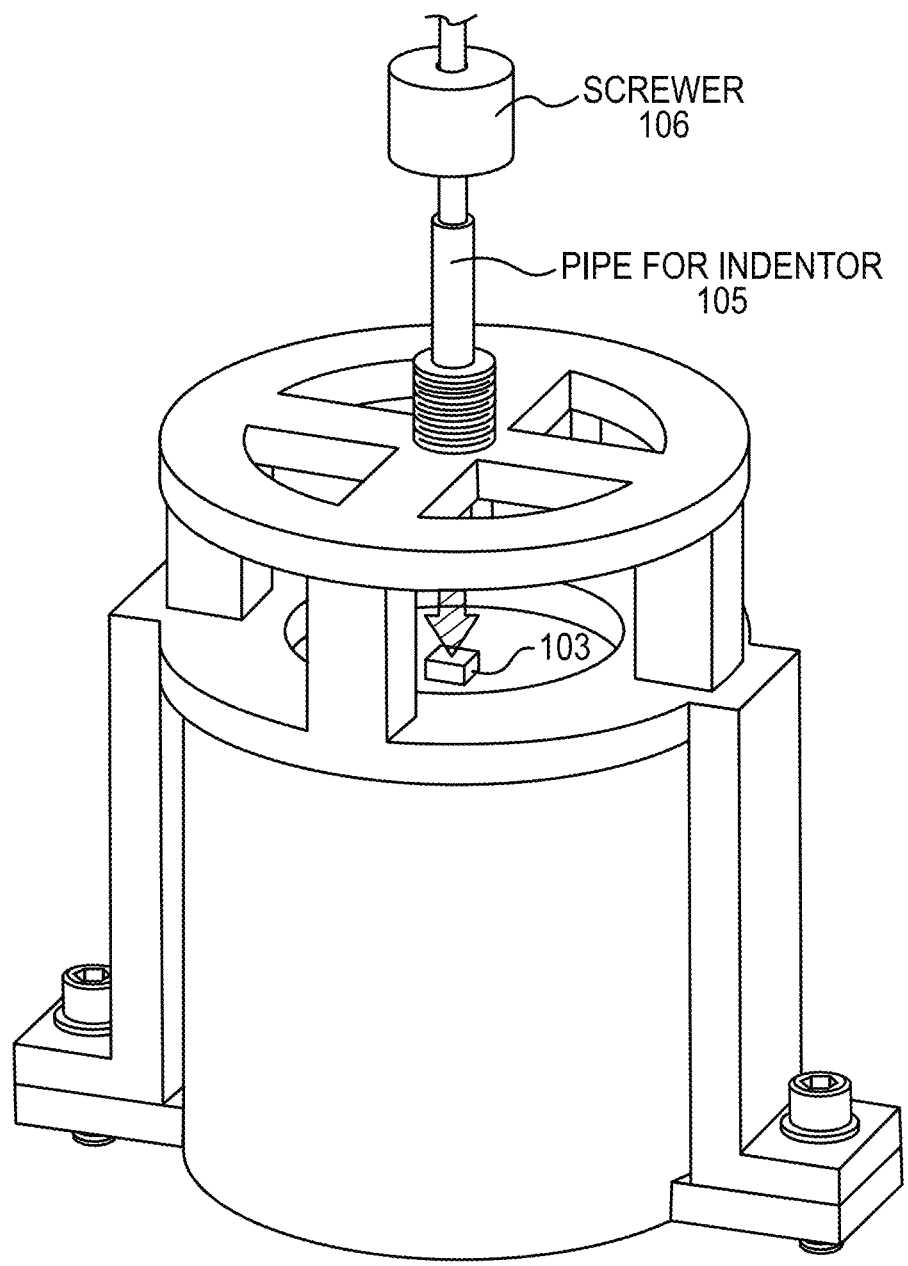
FIG. 15 is a perspective view of an indenter stage while inserting the pipe according to an exemplary aspect of the disclosure.
Figure 16:
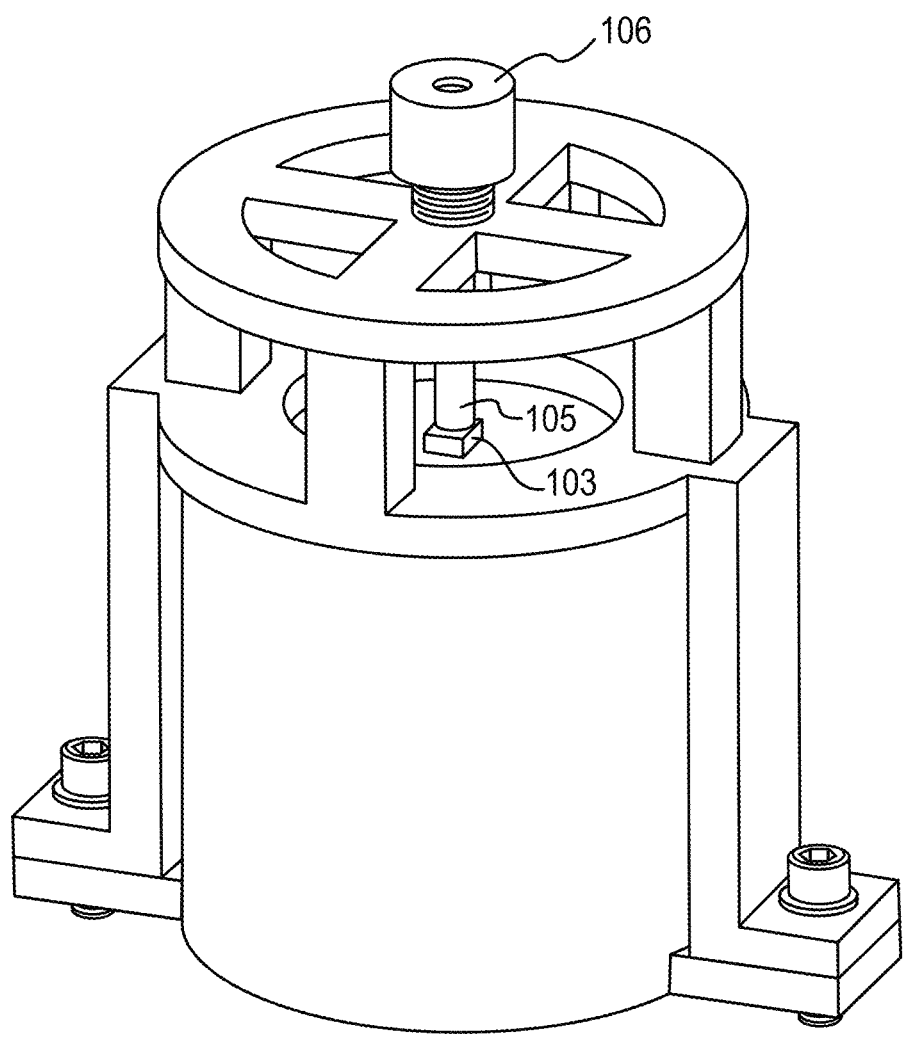
FIG. 16 is a perspective view of an indenter stage with the pipe positioned to hold the sample according to an exemplary aspect of the disclosure.
Figure 17:
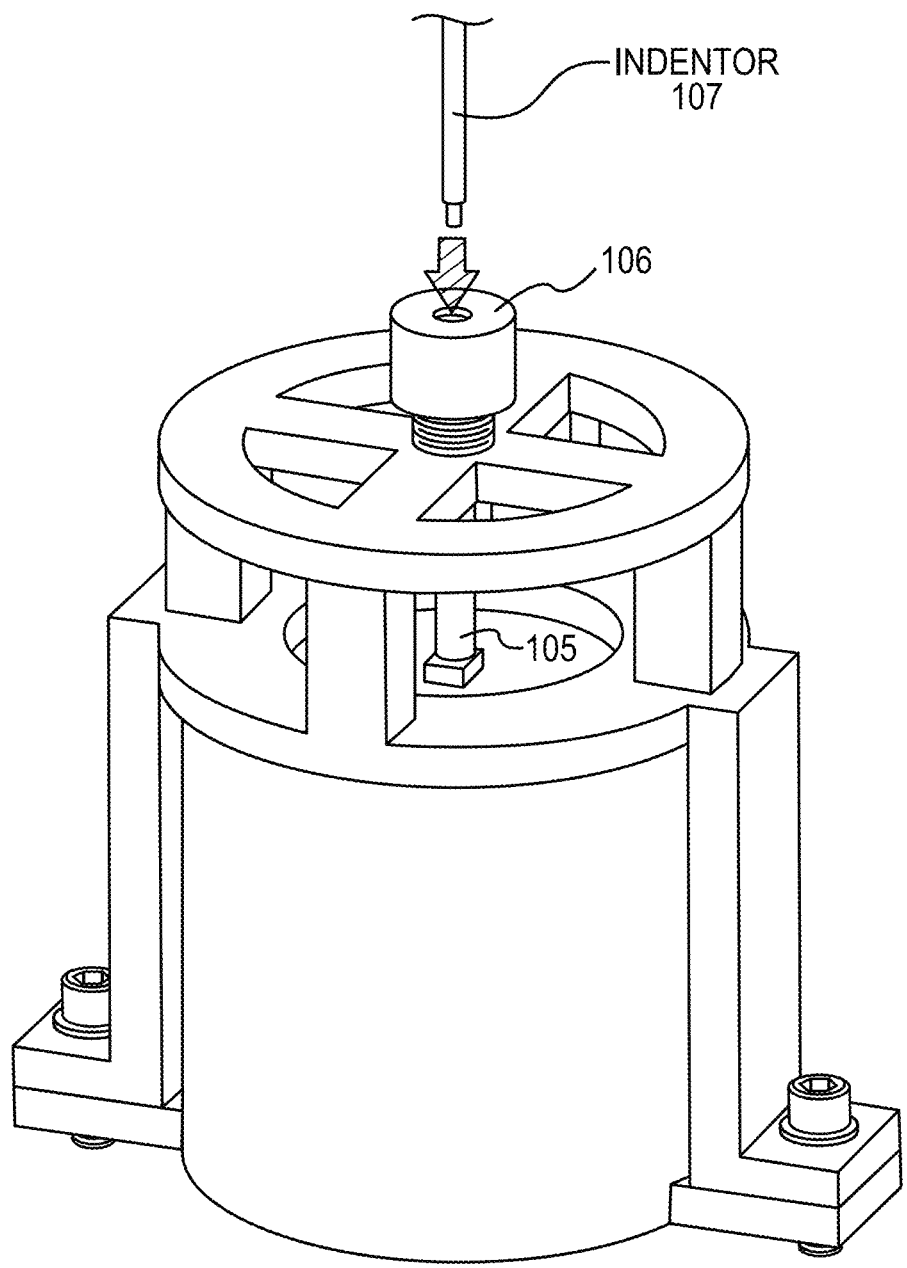
FIG. 17 is a perspective view of an indenter stage and the indenter according to an exemplary aspect of the disclosure.
Figure 18:
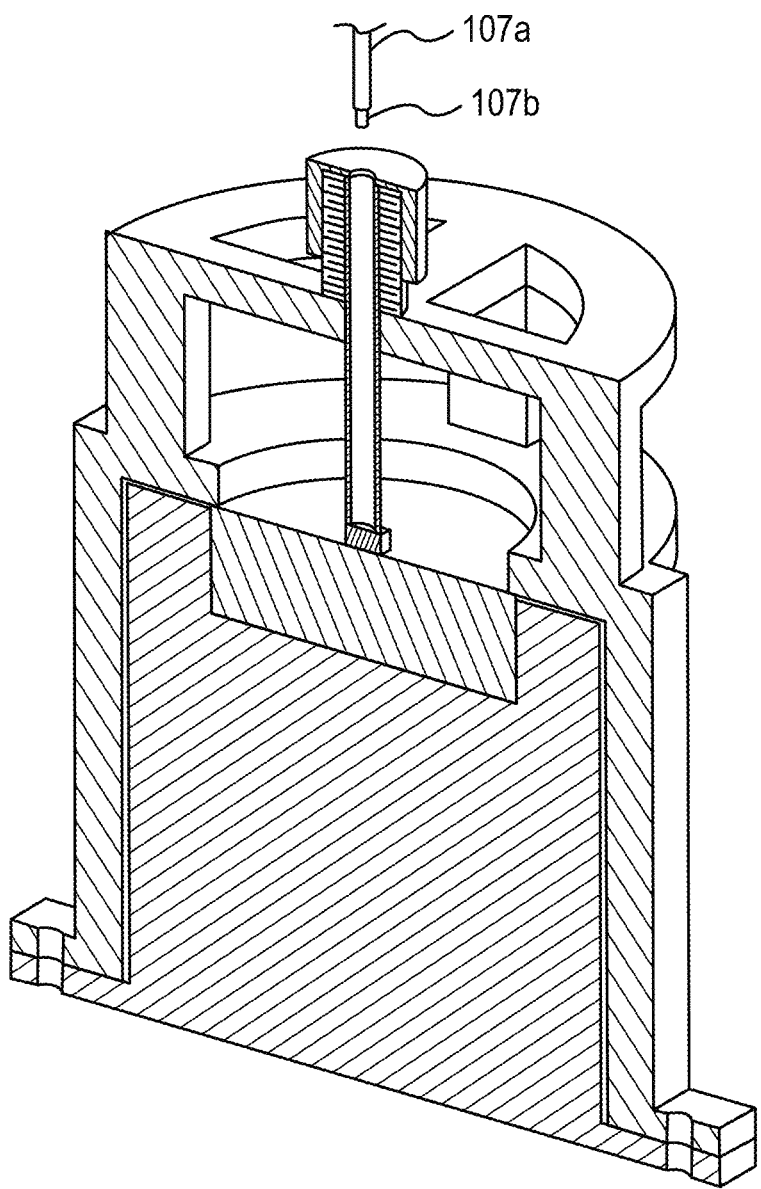
FIG. 18 is a perspective view of the indenter stage while the indenter is lowered into the pipe according to an exemplary aspect of the disclosure.
Figure 19:
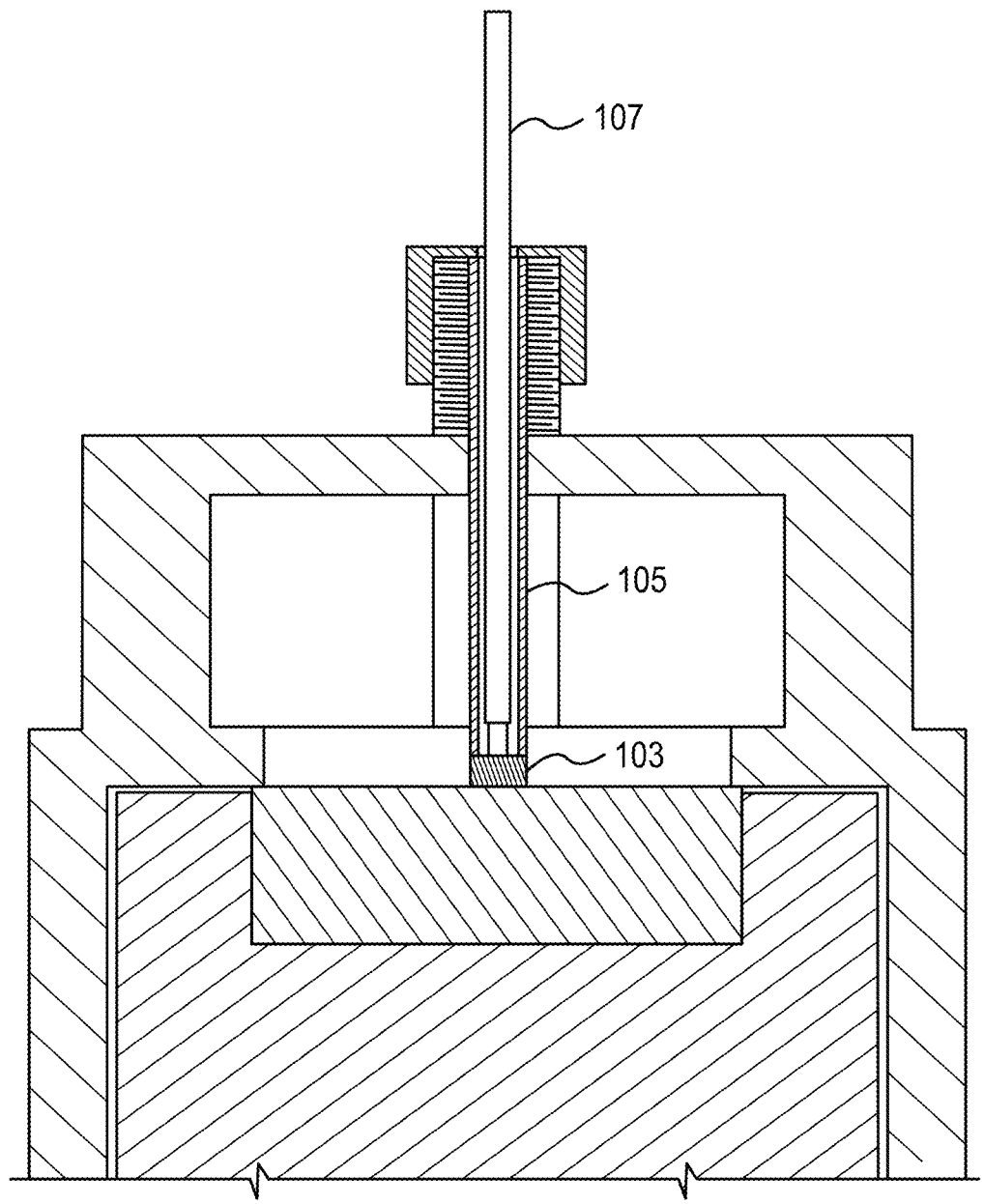
FIG. 19 is a perspective view of the indenter stage while the indenter is in contact with the sample according to an exemplary aspect of the disclosure.
Figure 20:
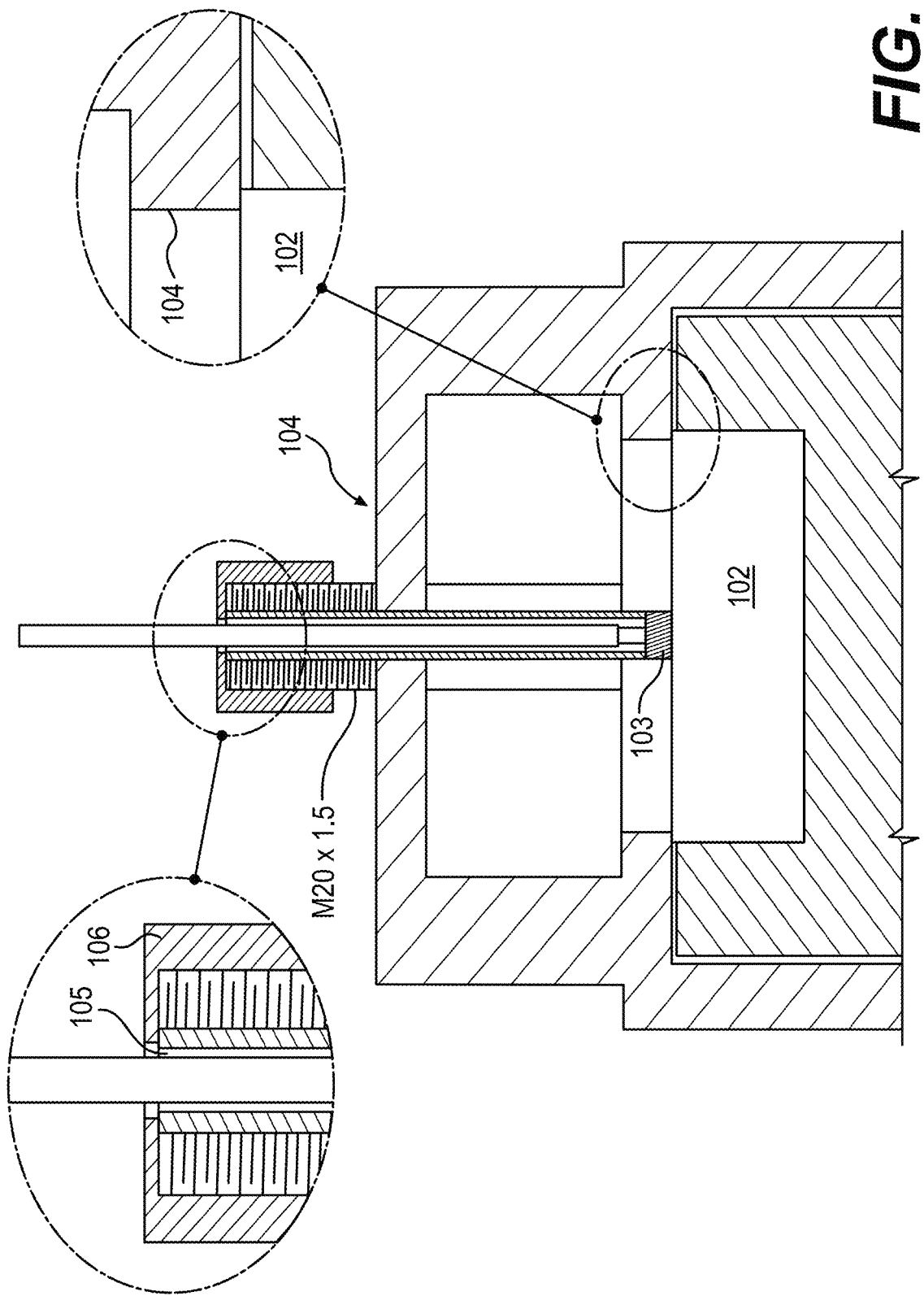
FIG. 20 is a perspective view of the indenter stage illustrating details of the thin cylindrical disc and the nut that presses the pipe according to an exemplary aspect of the disclosure.

In order to perform an indentation test, such as a high temperature micro-indentation test or a nano-indentation test, the crown 104 is fastened to the metallic cylindrical base 101. FIG. 8 is a perspective view of a cylindrical base 101 having a bolting configuration as shown in FIG. 5. FIG. 9 is a perspective view of the cylindrical base 101 illustrating a location where the thin cylindrical disc 102 will be inserted. FIG. 10 is a perspective view of the cylindrical base 101 having the inserted thin cylindrical disc 102. Next, as shown in FIG. 11, the crown 104 is connected to the cylindrical base 101 using a pair of bolts 108a, washers 108b, and nuts 108c. The bolts 108a, washers 108b, and the nuts 108c are used to clamp the crown 104 to the metallic cylinder 101, which in turn, clamps the cylindrical disc 102. FIG. 12 is a perspective view illustrating the crown 104 mounted to the cylindrical base 101. FIG. 13 is a perspective view illustrating a step of placing the sample 103 on an upper flat surface 102a of the cylindrical disc 102. FIG. 14 is a perspective view illustrating the indenter stage with the sample 103 positioned at the center of the thin cylindrical base 102. Next, as shown in FIG. 15, a high temperature resistant pipe 105 is inserted in an opening of the crown ring 104a and is pushed against the sample 103. The threaded nut 106 is placed on top of the ring 104a and, as shown in FIG. 16, presses the pipe 105 against the sample 103 by compressive force. An induction heating coil heats the sample 103 to about 1200° C. During high temperature indentation testing, the parts that are in contact with the sample must be brought into equilibrium such that their temperature is the same as that of the sample. Thus, heat is applied for several minutes to bring the sample and parts in contact with the sample into temperature equilibrium. FIG. 17 is a perspective view illustrating insertion of the indenter 107 into an opening in the nut 106 and into the pipe 105. FIG. 18 is a schematic illustrating the indenter being inserted, including a rod 107a and a tip 107b. As shown in FIG. 19, the indenter 107 contacts or penetrates the sample 103 based on test parameters. FIG. 20 is a perspective view illustrating a detailed view of the crown 104 applying pressure to the cylindrical disc 102 and a detailed view of how the nut 106 presses the pipe 105 as it is tightened in order to stabilize the sample 103.

Different magnitudes of displacement were considered such that the resulting clamping force is comparable to the present indenter stage. These displacement magnitudes are 0.01, 0.05, 0.1. 0.15 and 0.2 mm.

The well-known Norton's creep model, Eq. 1, is used $$\varepsilon = A\, \sigma^p t^q \tag{1}$$

where $\varepsilon$ is the creep strain, $\sigma$ is the stress, t is the time, and A, p, q are material constants as a function of temperature.

Norton's constants were obtained for high strength steel plate at temperatures, 27, 300, 400 and 500° C. only, and only these temperatures were analyzed in the finite element analysis.

Figure 26A:
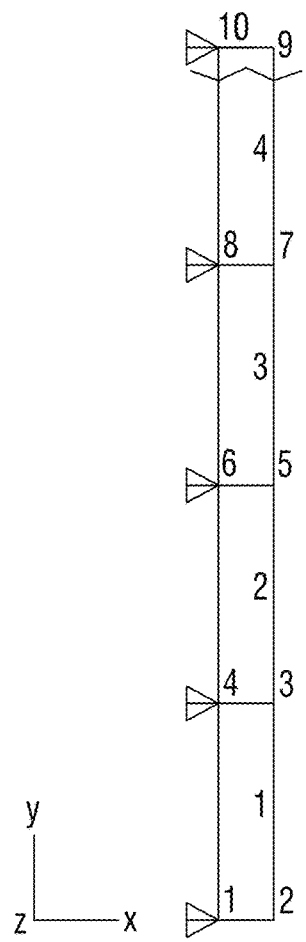
FIG. 26A shows mesh and boundary conditions of pipe.
Figure 26B:
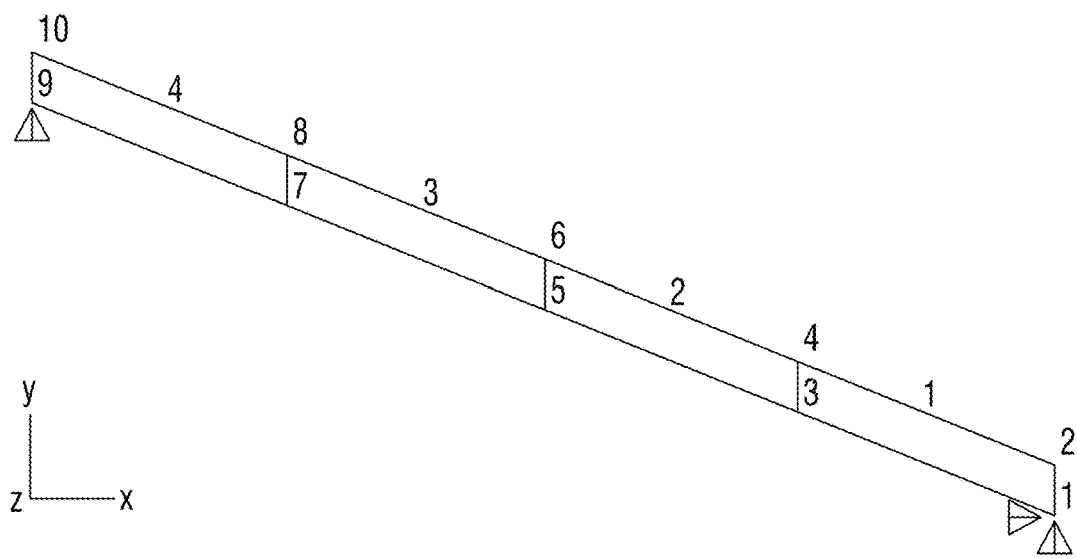
FIG. 26B shows mesh and boundary conditions of a conventional clamping mechanism.

The Norton's constant used in ANSYS software are listed in Table 1. The finite element models for the present indenter stage and the Anton Parr arrangement are shown in FIGS. 26A and 26B, respectively.

TABLE 1

Norton's creep constant at different temperatures.

| | Steel Properties | | | | | Constants used in ANSYS | | |
|---|---|---|---|---|---|---|---|---|
| | Temperature K (° C.) | E [GPa] | Yield [MPa] | True UTS [MPa] | K [Mpa] | C1 | C2 | C3 |
| 1 | 300 (27) | 208 | 298 | 590 | 792 | 3.4833E−14 | 4.505 | −0.72072 |
| 2 | 573 (300) | 170 | 254 | 660 | 886 | 2.1016E−14 | 4.505 | −0.72072 |
| 3 | 673 (400) | 157 | 231 | 532 | 713 | 5.5922E−14 | 4.505 | −0.72072 |
| 4 | 773 (500) | 143 | 203 | 390 | 523 | 2.2589E−13 | 4.505 | −0.72072 |

Figure 21:
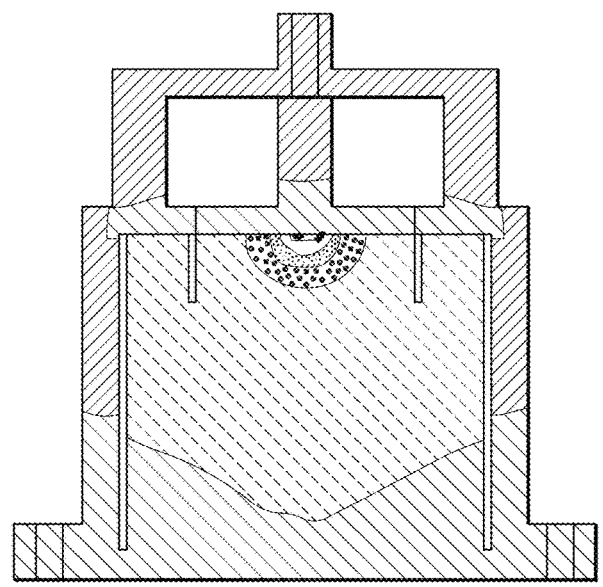
FIG. 21 is an image illustrating temperature distribution in the case of a steel base, according to an exemplary aspect of the present disclosure.
Figure 21:
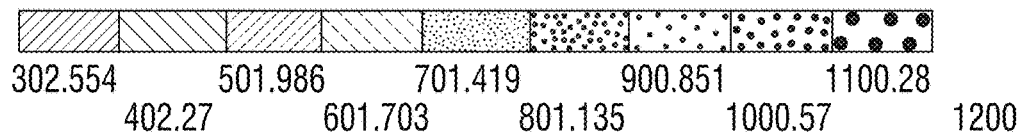
Figure 22:
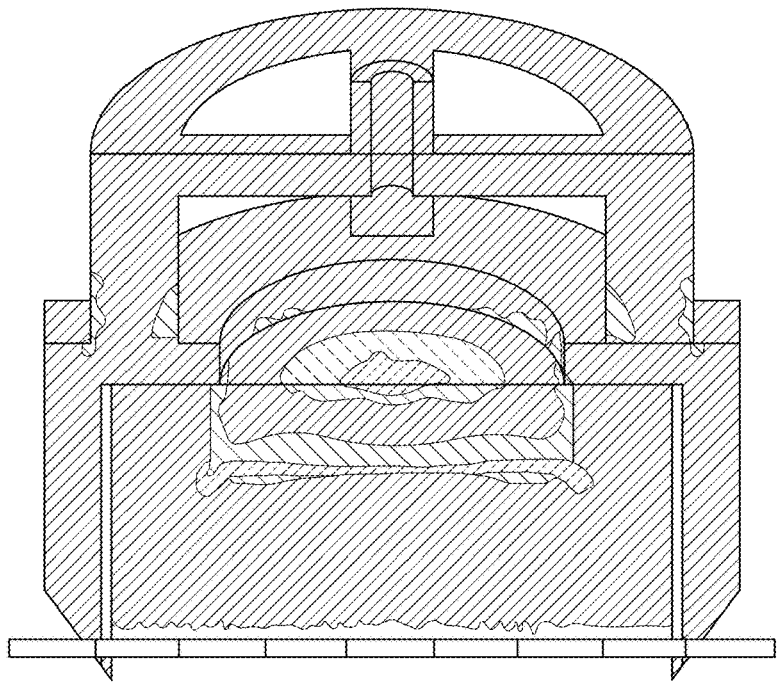
FIG. 22 is an image of von Mises equivalent stress distribution according to an exemplary aspect of the disclosure.
Figure 22:
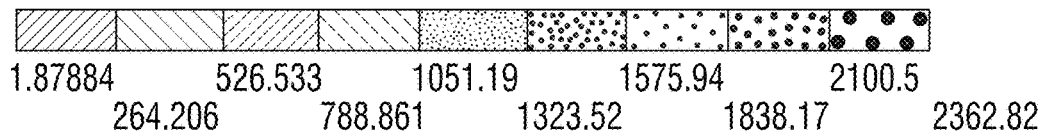
Figure 23:
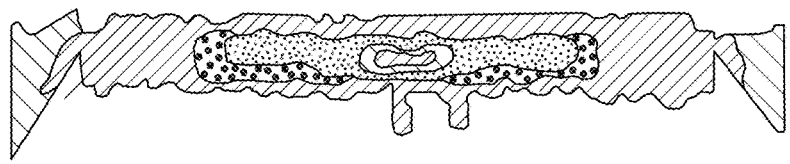
FIG. 23 is an image of von Mises equivalent stress in the case of a ceramic base, according to an exemplary aspect of the present disclosure.
Figure 23:
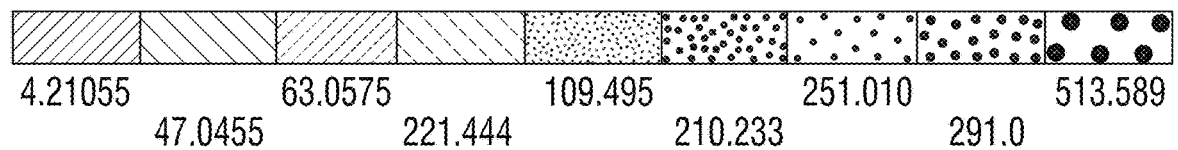
Figure 24:
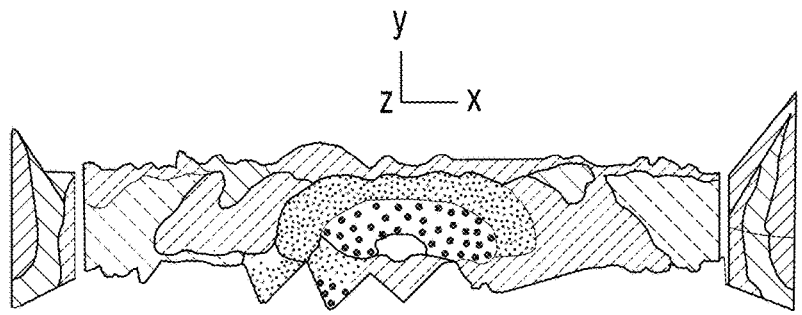
FIG. 24 is an image of von Mises equivalent stress in the case of a steel base.
Figure 24:
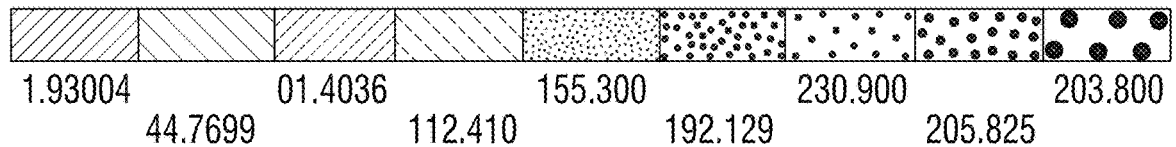

Finite element analysis was performed in order to verify the performance of an example indenter stage according to the present disclosure. However, the present disclosure is not limited to this example. FIG. 21 shows the heat distribution in an indenter having a ceramic plate 102 on a steel base 101. As can be seen in FIG. 21, the temperature for the steel base 101 is between 400 to 500° C. FIG. 22 shows the von Mises equivalent stress distribution. However, the high equivalent stress value in FIG. 22 is misleading because contact analysis between ceramic and steel was not defined. In the configuration used in FIGS. 21 and 22, the two pieces were glued and the resulting high stress was due to the deformation mismatch between the ceramic and the steel. Therefore, to have a more accurate understanding of the stress levels, focus was made on the ceramic and the top part of the steel base. The equivalent stress distribution for the ceramic 102 and the steel base 101 are shown in FIGS. 23 and 24, respectively. These two figures show that the stress level is in the range of 350 MPa, which is low.

A major cause of failure in designs is creep. Thus, analysis was performed for creep. Creep analyses were performed using ANSYS software. Comparative analysis was made for Anton Parr GmbH High Temperature Ultra Nonintention Tester UNHT HTV.

Figure 25A:
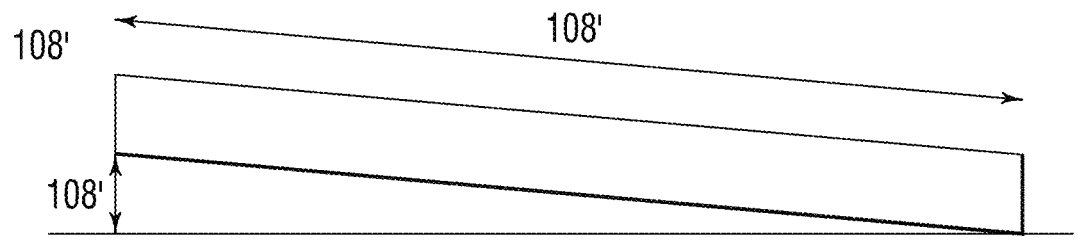
FIG. 25A shows a model of a conventional clamping mechanism.
Figure 25B:
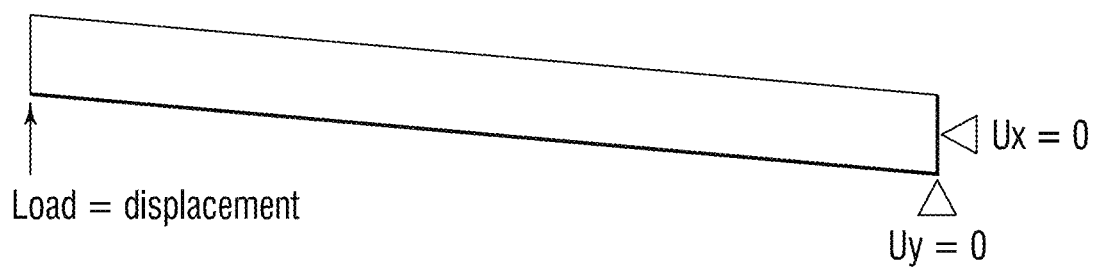
FIG. 25B shows loading and boundary conditions of a conventional clamping mechanism.

The analysis for the Anton Parr Tester included applying a clamping force by bending loading. A wedge applied clamping force as the crown is advanced into higher pin position. The clamping wedge was modeled as a 2D plain strain plate and its dimensions were roughly estimated based on the arrangement as shown in FIG. 25A. The loading and boundary conditions for this wedge are shown in FIG. 25B.

Static analyses were performed on both arrangements to investigate the relation between the applied force and resulting displacement. Table 2 shows the resulting von Mises stresses and the displacements from the application of 1, 2, 3 and 4 N. Similarly, Table 3. Shows the resulting von Mises stresses and reactions from the application of 0.01, 0.05, and 0.1 mm. It can be seen from Table 2 that a force of 4N will result in 0.1049E-3 mm of displacement at the location of applied force. Therefore, creep analysis on Model A (the present indenter stage) was performed under displacement controlled with applied value of 0.1049E-3 mm. This value is corresponding to an applied force of 4N which is high in magnitude. However, it will still be used as the worst-case scenario.

TABLE 2

Static analysis on Model (A)-the submitted design.

| Load [N] | von Mises Stress [MPa] | | | Displacement [mm] | |
|---|---|---|---|---|---|
| | Node 9 | Node 10 | Max. Node 3 | Node 9 | Node 10 |
| 1 | 0.064248 | 0.63196 | 0.72919 | 0.26228E−4 | 0.26232E−4 |
| 2 | 0.12850 | 0.12639 | 0.14584 | 0.52456E−4 | 0.52464e−4 |
| 3 | 0.19274 | 0.18595 | 0.21876 | 0.78684E−4 | 0.78696E−4 |
| 4 | 0.25699 | 0.25279 | 0.29167 | 0.10491E−3 | 0.10493E−3 |

The analysis on Model B (the Anton Parr Tester) design was performed under displacement controlled with a value of 0.01 mm. As listed in Table 3, this displacement value will generate a reaction in the negative y-direction of about 0.37 N which is basically the clamping force. This is a low value.

However, the analysis is performed to show that even though conservative values were considered for the Anton Parr Tester it is still not better than the submitted design.

TABLE 3

Static analysis on Model (B)-the Anton Parr Tester. von Mises stress exceeded the yield strength at 0.15-0.2 mm.

| Applied displacement | Von Mises stress At node 2 | Reactions Rx [N] | Ry [N] |
|---|---|---|---|
| 0.01 | 15.334 | 17.212 | −0.37135 |
| 0.05 | 76.670 | 86.059 | −1.8567 |
| 0.1 | 170.05 | 172.12 | −3.7135 |

As mentioned previously, necessary creep constants were only obtained at a maximum temperature of 773 K (500° C.). The test will run for one complete hour.

Figure 27A:
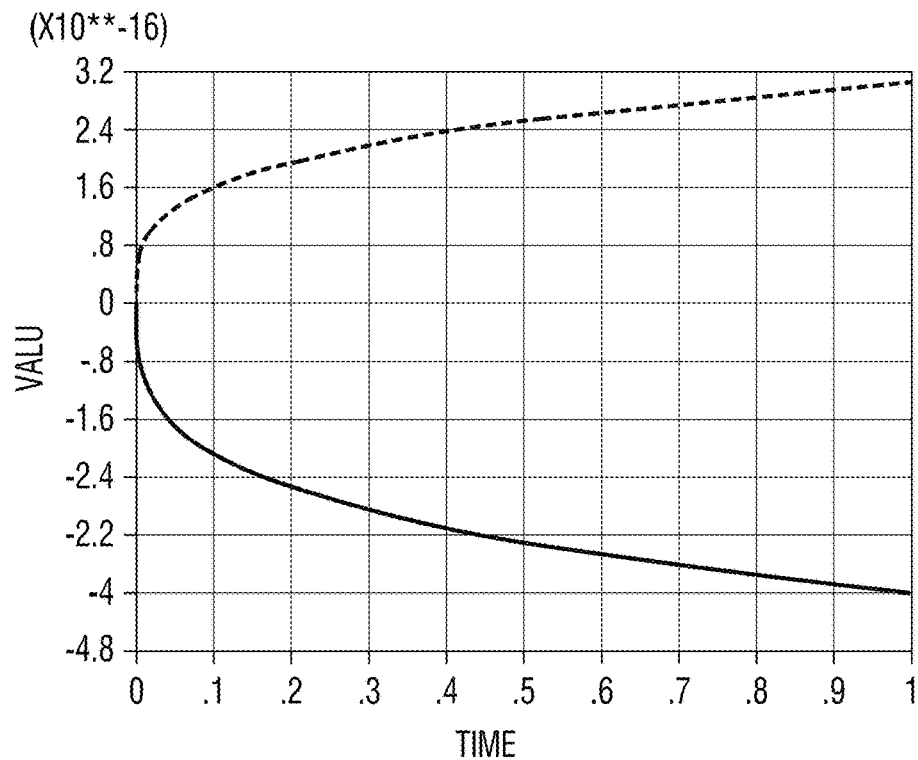
FIG. 27A shows a plot of creep strain over time for current invention.
Figure 27B:
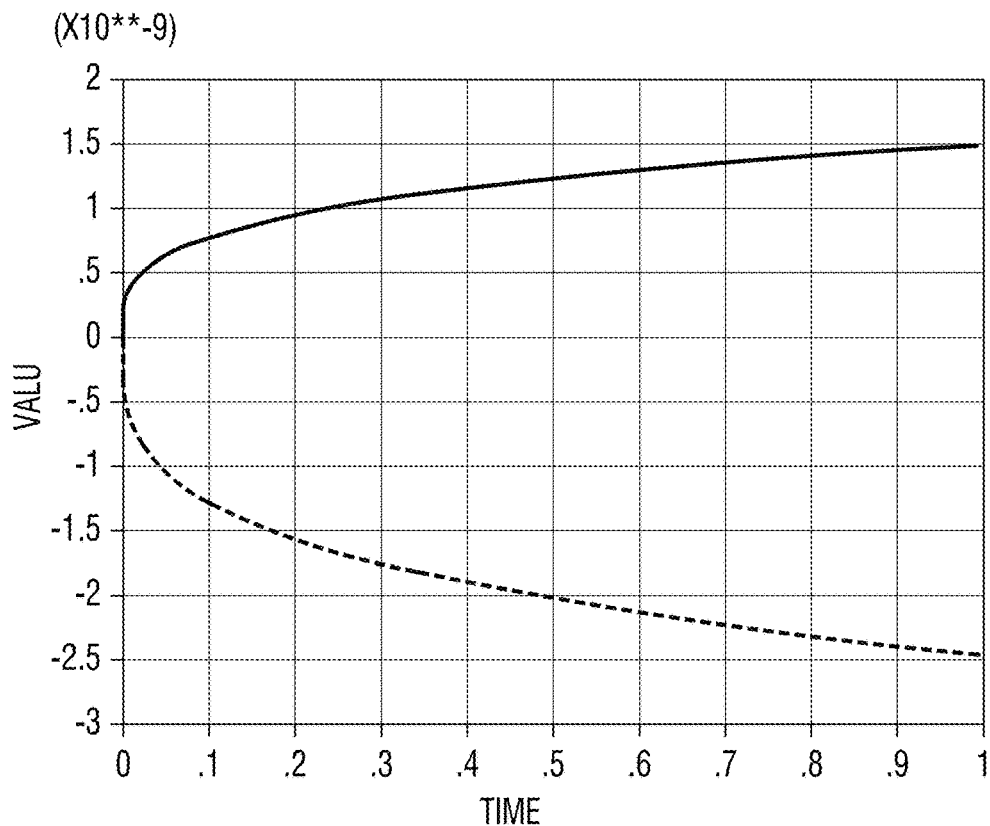
FIG. 27B shows a plot of creep strain over time for a conventional clamping mechanism.
Figure 28:
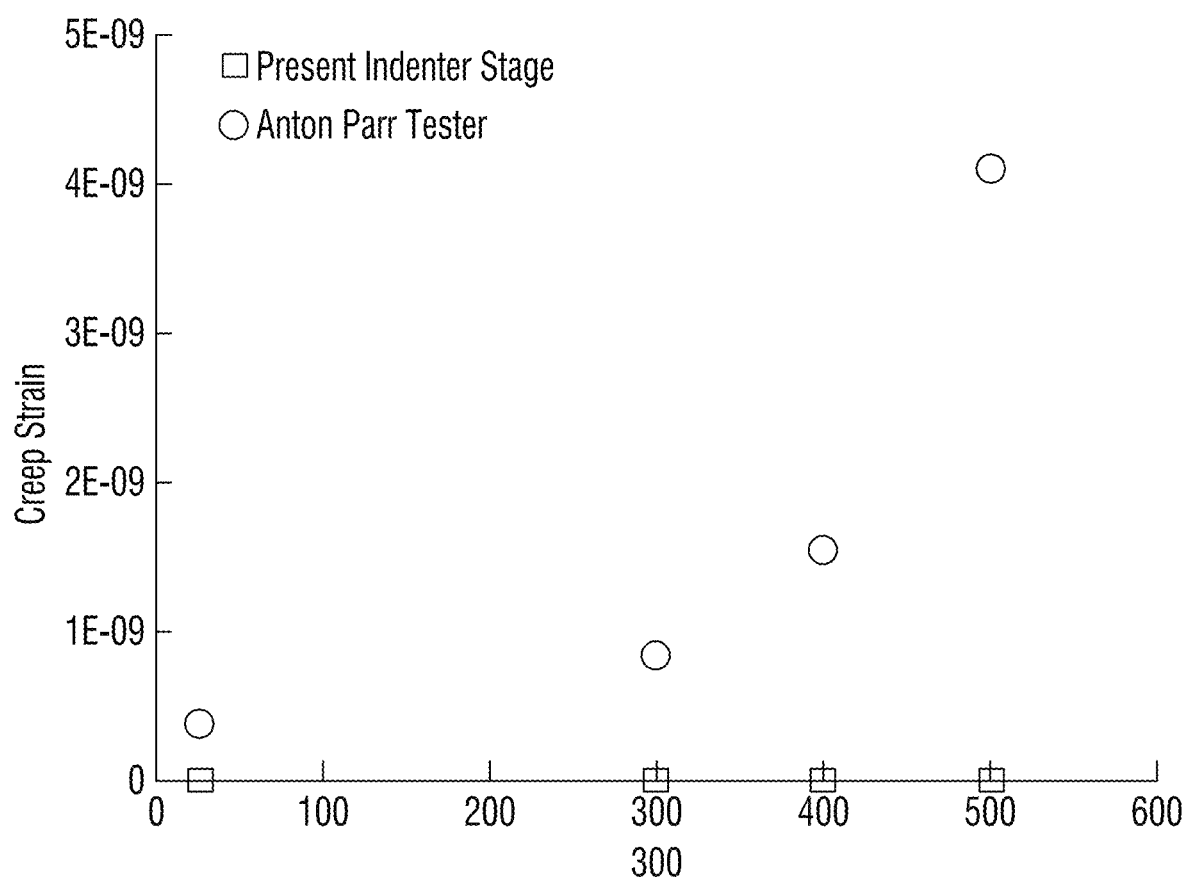
FIG. 28. shows a comparison of creep strain vs. temperature for current invention and a conventional clamping mechanism.

The evolution of creep strain in x- (EPCRX) and y- (EPCRY) directions for the present indenter stage and Anton Parr Tester are shown in FIGS. 27A and 27B, respectively. The time (x-axis) is measured in hours. In addition, Table 4 lists the numerical values of the creep strain at the critical locations for both designs and at different temperatures. To recognize the differences between present indenter stage and Anton Parr Tester the data in Table 4 are plotted in FIG. 22. It is clear from FIG. 28 that the present indenter stage is significantly more resistant to creep than the Anton Parr Tester.

TABLE 4

Creep results for: Model (A): present indenter stage and Model (B) Anton Parr Tester.

| Temperature K (° C.) | Node | von Mises Creep Strain |
|---|---|---|
| Model A | | |
| 300 (27) | 3 | 0.44923E−15 |
| 573 (300) | 3 | 0.10923E−15 |
| 673 (400) | 3 | 0.20310E−15 |
| 773 (500) | 3 | 0.53862E−15 |
| Model B | | |
| 300 (27) | 2 | 0.36878E−09 |
| 573 (300) | 2 | 0.82739E−09 |
| 673 (400) | 2 | 0.15384E−08 |
| 773 (500) | 2 | 0.40796E−08 |

The critical components in both approaches are used to apply clamping force on the sample. Because the sample is heated at certain temperature these components must be equilibrated such that their temperatures are very close to the sample. As the clamping force must be kept constant during the test, the critical components will be prone to failure due to creep damage.

The well-known Norton's creep law was used; the obtained results clearly show that the present indenter stage is significantly better than that by Anton Parr Tester.

It was assumed that both designs are made of the same materials. Although this assumption is conservative and in favor to the Anton Parr Tester because the submitted design can easily be made of ceramic material that should have significantly better performance in high temperature applications.

The indenter stage of the present disclosure is better than the Anton Parr Tester. The indenter stage of the present disclosure is made of ceramic material which can handle compressive loading. Conversely, the Anton Parr Tester applies clamping by bending which generates tensile and compressive stresses. These forces can each be individually eliminated using the indenter stage of the present disclosure. Ceramics are weaker in tension than in compression making the application of ceramics in Anton Parr Tester less likely (if not impossible). Also, using ceramics in a high temperature application is preferable because of its durability, which is better than that of alloys.

A system which includes the features in the foregoing description provides numerous advantages. In particular, the disclosed stage, and particularly the approach to clamping, should enable micro- and nano-indentation testing at high temperature reaching to, and exceeding, 1200° C.

Numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An indentation tester for testing a sample heated at a heating temperature above 800° C. to 1200° C., the indentation tester comprising:
    a stage including an outer base that houses an inner base made of a temperature resistant material sufficient to maintain shape at the heating temperature;
    a removable crown that fastens to the outer base,
    wherein the removable crown includes a support that holds an axisymmetric pipe made of a temperature resistant material sufficient to maintain shape over the range of heated temperature,
    wherein the axisymmetric pipe guides an indenter to penetrate the sample,
    wherein the removable crown includes a first rim that has a central threaded ring mated with a threaded nut and tightening the nut places a compressive force on the pipe and the compressive force presses the axisymmetric pipe which pushes against the sample to secure the sample in place.

2. The indentation tester of claim 1, wherein the first rim includes an outer rim that is attached to the threaded ring by spokes spaced at equivalent angles between adjacent spokes, and legs projecting from the outer rim at positions corresponding to the spokes, wherein at least two opposing legs are fastened to the outer base.

3. The indentation tester of claim 2, wherein a top portion of the inner base is elevated above the top of the stage such that the crown presses against the inner base.

4. The indentation tester of claim 1, wherein the support that holds the pipe is ceramic.

5. The indentation tester of claim 1, wherein the outer base is a metallic base.

6. The indentation tester of claim 1, wherein the indenter includes a rod made of the temperature resistant material and a tip attached to the rod.

7. The indentation tester of claim 6, wherein the tip is made of diamond with pyramid, wedge, cone, cylinder or sphere shape.

8. The indentation tester of claim 1, wherein the indentation tester is a nano-indenter.

9. The indentation tester of claim 1, wherein the indentation tester is a micro-indenter.

\* \* \* \* \*